United States Patent [19]

Clay

[11] Patent Number: 5,038,624
[45] Date of Patent: Aug. 13, 1991

[54] SOIL RECORING DEVICE

[75] Inventor: Val E. Clay, Blue Springs, Mo.

[73] Assignee: Mobay Corporation, Pittsburgh, Pa.

[21] Appl. No.: 483,183

[22] Filed: Feb. 21, 1990

[51] Int. Cl.⁵ .......................... G01N 1/08; G01N 1/28; E21B 49/02
[52] U.S. Cl. .................................... 73/864.44; 73/863
[58] Field of Search .......... 73/864.44, 864.45, 864.41, 73/863; 175/58

[56] References Cited

U.S. PATENT DOCUMENTS

| | | | |
|---|---|---|---|
| 3,075,588 | 1/1963 | Mitchell | 175/20 |
| 3,162,256 | 12/1964 | Meinecke | 175/252 |
| 3,324,958 | 6/1967 | Clark | 175/84 |
| 3,457,778 | 7/1969 | Gill et al. | 73/84 |
| 3,631,934 | 1/1972 | Rocha | 175/58 |
| 3,872,935 | 3/1975 | Mielke | 175/58 |
| 3,894,588 | 7/1975 | Brill | 175/19 |
| 3,964,555 | 6/1976 | Franklin | 175/44 |
| 3,978,932 | 9/1976 | Mielke | 175/249 |
| 4,081,040 | 3/1978 | Henson | 175/58 |
| 4,106,576 | 8/1978 | Clements | 73/864.44 X |
| 4,372,174 | 2/1983 | Lymbalisty et al. | 73/864.41 X |
| 4,458,525 | 7/1984 | Lutenegger et al. | 73/84 |
| 4,483,197 | 11/1984 | Kellner | 73/784 |
| 4,653,336 | 3/1987 | Vollweller | 73/864.44 |
| 4,685,339 | 8/1987 | Philipenko | 73/864.45 |

FOREIGN PATENT DOCUMENTS

| | | | |
|---|---|---|---|
| 16048 | 8/1964 | Japan | 73/864.44 |
| 960571 | 9/1982 | U.S.S.R. | 73/864.44 |
| 918090 | 2/1963 | United Kingdom | 73/864.45 |

Primary Examiner—Tom Noland
Attorney, Agent, or Firm—Joseph C. Gil; Lyndanne M. Whalen

[57] ABSTRACT

A device for recoring soil samples composed of a device for advancing a soil sample, a soil sample assembly, a cutting tube and a chamber for receiving the soil sample as it exits the cutting tube. The cutting tube has a diameter which is smaller than that of the original soil sample which is to be recored.

7 Claims, 2 Drawing Sheets

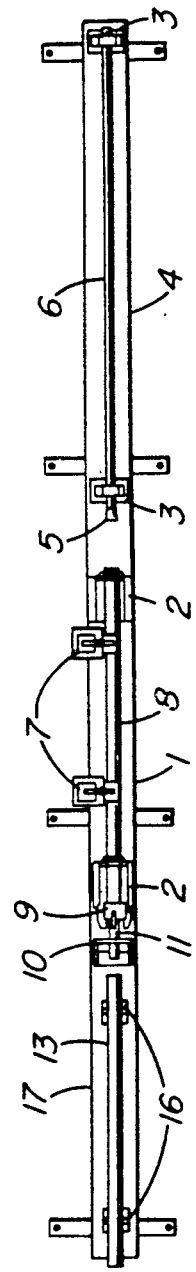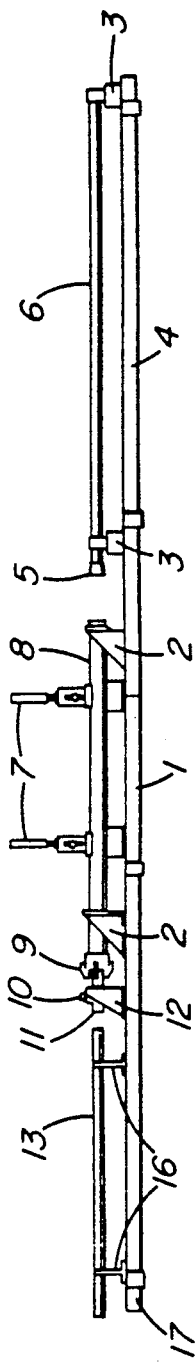

SOIL RECORING DEVICE

BACKGROUND OF THE INVENTION

The present invention relates to a device for recoring soil samples and to a method for recoring soil samples in which this device is employed.

Core samples of soil are collected for a variety of reasons. For example, core sampling is an important preliminary in the construction industry. Such core samples are typically taken to determine the ability of the soil to handle water and the type of foundation needed to support a structure.

Core sampling is also important for the agricultural industry. Such sampling is used to analyze moisture content, nutrient content, etc. Another reason for gathering such samples is to determine the extent to which pesticides have affected the soil to which they have been applied either directly or indirectly through application to plants or crops and also to determine whether those chemicals have reached the water table.

Many devices and techniques for gathering such soil samples have been developed and used over the years. Examples of such devices include those disclosed in US Pat. No(s) 3,075,588; 3,162,256; 3,324,958; 3,457,778; 3,631,934; 3,872,935; 3,894,588; 3,964,555; 3,978,932; 4,081,040; 4,458,525; 4,483,197 and 4,653,336. One technique commonly employed today to gather such core samples is to insert a plastic liner into a steel tube which steel tube is forced into the ground for a predetermined depth. The steel tube is then removed from the ground and the soil contained in the plastic liner is removed and analyzed. This commonly used technique may, however, produce inaccurate results if the pesticide residue present at or near the soil surface is carried by the steel tube and/or the plastic liner to the deepest test point.

This same problem exists with each of the devices disclosed in the above-listed patents.

It would therefore be advantageous to have a device and/or method for removing such falsely contaminated soil from a core soil sample before analysis of the sample was begun.

SUMMARY OF THE INVENTION

It is an object of the present invention to provide a device for removing the outer surface soil of a core sample.

It is also an object of the present invention to provide a device for removing a soil core sample from a core sample.

It is another object of the present invention to provide a device for taking core samples which core samples do not include soil contaminated by pesticide which was carried from the surface by the coring device and/or the liner present therein to the deepest test point.

It is a further object of the present invention to provide a method for collecting soil core samples which have not been falsely contaminated with pesticide present only at surface level prior to taking of the core sample.

These and other objects which will be apparent to those skilled in the art are accomplished by using a recoring device made up of a base, a cutting tube having a diameter which is smaller than that of the sample to be recored and which is fixed to the base, a means for advancing a tube containing the soil sample to be recored in a manner such that the inner portion of the soil sample passes through the cutting tube and a receptacle for soil exiting the cutting tube. In using this device, a soil core which has been collected in accordance with known techniques and stored in a tube which is generally plastic is first attached to the means for advancing such sample through the cutting tube. The soil core is positioned in the sample tube assembly in a manner such that the soil core will be recored from the bottom to the top (i.e., the soil taken from the deepest point of the test location will pass through the cutting tube first). This is done because the soil taken from the deepest point of the test location will generally contain less pesticide residue than soil taken at or near the surface. Recoring from the bottom to the top makes it less likely that any residual pesticide present in the soil taken from near the surface will contaminate the soil taken from deeper points and produce false results. The advancing means is then activated and the soil core is passed through the cutting tube. As the original soil core passes through the cutting tube, the plastic tube in which that core was stored is cut away as is an outer layer of the soil present on the circumference of the original core. Since pesticide carried from the surface to the test site is present on the storage tube and in the soil present on the outer surface of the soil core, these materials are discarded. The remaining portion of the soil core which exits the cutting tube is deposited in a receptacle in a manner such that the core remains intact. This smaller core is essentially free of any contaminants carried from the surface. Analysis of this core will therefore more accurately reflect the residual features of a pesticide.

BRIEF DESCRIPTION OF THE DRAWINGS

FIG. 1 is a top view of the recoring device of the present invention.

FIG. 2 is a side view of the recoring device of the present invention.

DETAILED DESCRIPTION OF THE PRESENT INVENTION

Figure 3:
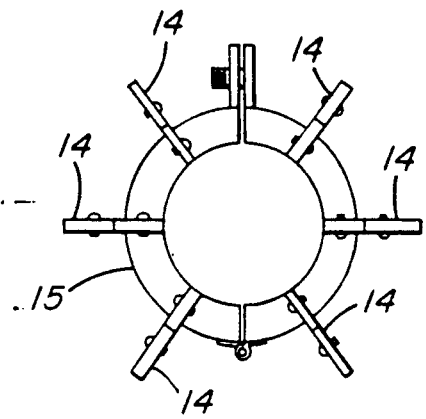
FIG. 3 is a front view of the collar assembly of the cutting tube of the recoring device of the present invention.

Devices for removing a core sample of soil from a selected location are known and commercially available. One example of such a device is Giddings Machine Company's hydraulic coring and sampling device.

Any one of the known coring devices may be used to obtain the soil sample which is to be recored in accordance with the present invention as long as the sample collected using that device is encased in a liner made of a durable but easily removed material. Plastics are preferred encasing materials. Soil samples encased in a durable plastic liner are the preferred starting materials for the recoring device of the present invention because they maintain the integrity of the sample prior to the recoring operation but may be readily removed during the recoring operation.

The recoring device of the present invention is composed of a cutting tube which remains stationary during the recoring operation, a means for advancing a soil sample encased in a sample tube in a manner such that the cutting tube will pass through the central portion of sample tube and a receptacle in which the soil sample is collected intact as it exits the cutting tube. An illustration of one such device is given in FIGS. 1 and 2. FIG. 1 is a top view of the recoring device and FIG. 2 is a side view of this same device. This illustrated device will be discussed in specific detail for purposes of illustration only. The reference numbers common to both FIGS. 1 and 2 identify the same element of the device. Variations of this device which are within the scope of this invention will be obvious to those skilled in the art.

Each section of the device of the present invention may be mounted to the same base or each section may have its own base which may be connected to the base for each of the other two sections. In FIGS. 1 and 2 three base sections which are connected are illustrated. This illustrated embodiment is advantageous because the recoring device is much more portable than a device mounted to a base composed of one integral sheet of a material such as stainless steel.

As can be seen from FIG. 2, the means for advancing a sample tube assembly 8 containing a tube filled with soil to be s tested is hydraulic piston 6 which is mounted to hydraulic base 4 by means of hydraulic mount 3. In the apparatus illustrated in FIGS. 1 and 2, a cone 5 made of stainless steel is mounted on the end of hydraulic piston 6 to cushion the impact when the hydraulic piston 6 comes into contact with sample tube assembly 8. This cone may however be omitted. Any apparatus capable of moving sample tube assembly 8 from its starting position over cutting tube 11 in a manner such that a sample will be taken from the inner diameter of the original sample placed in sample tube assembly 8 would, however, be appropriate.

The soil sample contained in a liner or tube composed of a material such as plastic which is to be recored is placed in sample tube assembly 8 which is positioned to the same height as cutting tube 11 by sample tube assembly supports 2. Sample tube assembly 8 is held in place before the recoring operation is begun by sample tube clamp assemblies 7 which are mounted to sample tube base 1. Once the sample has been secured via clamps 7, the hydraulic piston 6 is actuated and the sample tube is pushed forward so that the sample's central portion passes through cutting tube collar assembly 9 and cutting tube 11. Cutting tube 11 is held in position by means of clamp 10 and cutting tube support 12. Since the diameter of cutting tube 11 is less than that of the sample tube, the outer portion of the original soil sample and the sample tube which do not pass through the cutting tube 11 are shaved away by both the cutting device present in cutting tube collar assembly 9 and cutting tube 11. The portion of the soil and the cut away plastic tube are discarded. The recored sample exiting cutting tube 11 is collected intact in receiving chamber 13. Receiving chamber 13 is a tube made of a blend of Teflon resin and glass which sits on an adjustable cradle assembly 16 which is mounted on base 17. After the entire soil sample has passed through cutting tube 11, receiving chamber 13 is opened and the soil sample present therein is segmented. These segments may then be analyzed or packaged and sent to a lab for analysis.

Sample base 1, hydraulic base 4 and receiving chamber base 17 were made of steel but any durable material, particularly metals such as stainless steel may be employed. As was mentioned above, it would be possible to use a single base for mounting sample tube assembly 8, hydraulic cylinder 6 and receiving chamber 13 where the recoring device need not be movable such as where the device is to be used in a single, permanent location (e.g., in a laboratory). Sample tube support 2, hydraulic cylinder mount 3, sample tube clamp assembly 7, clamp 10, cutting tube support 12 and cradle assembly 16 may be made of any of the materials in which they are commercially available. Stainless steel is particularly preferred.

Hydraulic piston 6 is made of a durable material such as steel. Sample tube assembly 8 is made of a material such as stainless steel and has an inner diameter of 4.5 cm. The inner diameter of sample tube assembly 8 is selected so that it will be at least 0.5 cm greater than the outer diameter of cutting tube 11, preferably from about 0.5 to about 2.0 cm greater and most preferably from about 0.7 to about 1.0 cm greater than that of cutting tube 11.

Figure 4:
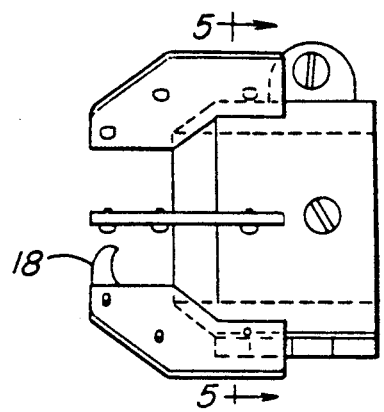
FIG. 4 is a side view of a blade assembly for the collar assembly shown in FIG. 3.
Figure 5:
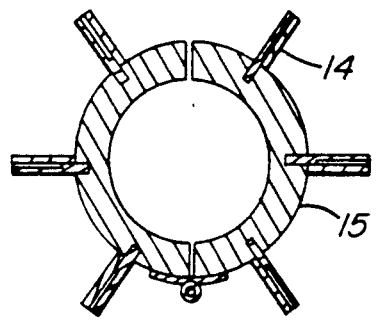
FIG. 5 is a cross section of the blade assembly shown in FIG. 4.
Figure 6:
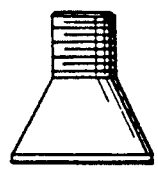
FIG. 6 is a side view of a boring cone useful in the recoring device of the present invention.
Figure 7:
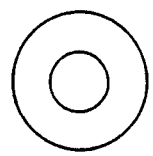
FIG. 7 is a bottom view of the boring cone shown in FIG. 6.

Cutting tube collar assembly 9 is more clearly shown in FIG. 3 in which six cutting blade assemblies 14 are positioned equi-distant around the circumference of the collar 15. Collar 15 is made of steel but could also be made of any so other durable material such as stainless steel. A cutting blade assembly 14 is illustrated in FIG. 4 in which cutting blades 18 were made of commercially available steel utility blades.

Cutting tube 11 was made of stainless steel but could be made of any material capable of slicing off the outer portion of the soil sample placed in sample tube assembly 8 and the liner or tube in which it is present. Preferred materials from which cutting tube assembly 11 could be made include: steel, copper, brass and aluminum.

Receiving chamber 13 is a tube made of a blend of Teflon resin and glass having a diameter large enough to receive the recored soil sample without disturbing its integrity. This receiving chamber could also be made of any material to which soil will not adhere so that the sample will move along the chamber as more soil exits cutting tube 11 and remain intact. Examples of such materials include: plastics, aluminum, brass, steel, stainless steel and copper.

In practicing the process of the present invention with the device illustrated in FIGS. 1 and 2, the soil sample contained in a plastic liner is placed in soil sample assembly 8 and clamped in position with sample tube clamp assembly 7 in a manner such that the bottom of the soil sample (i.e., the portion of the sample taken at the deepest point of the test site) will pass through cutting tube 11 first. Hydraulic piston 6 is actuated and begins to move forward. Cone 5 comes into contact with the soil inside sample tube assembly 8 which is then pushed forward so that the soil sample and the liner pass through cutting tube collar assembly 9 and cutting tube 11 until the entire soil sample has passed through cutting tube 11 and been deposited in receiving chamber 13.

Having thus described my invention, the following Examples are given as being illustrative thereof.

EXAMPLES

In order to determine the effectiveness of the recoring device of the present invention, fluorescein dye was dispersed over the surface of the area where a soil core was to be taken. The soil core was then collected using a split barrel sampler (sold by Gidding Machine Co., Fort Collins, Co.) with an acetate liner. The core sample in the acetate liner was removed from the coring device and visually inspected. The fluorescein dye could be seen in soil from the top (surface) down to about ¾ the length of the four foot (1.2 m) long sample. The presence of this dye below surface level clearly indicated that the dye which was initially present on the surface had been carried down almost three feet (0.9 m) from the soil surface by the core sampling device. The same observation was made with respect to all samples which had not been recored.

A number of samples were collected in the same manner as described and then recored using the device illustrated in FIGS. 1 and 2 and described in detail above. The recoring device was cleaned with acetone between samples. Each of the recored samples was then broken down into sections of approximately 6 inches (0.15 m). Each section was then analyzed spectrophotometrically for fluorescein content as follows. Each sample section was air dried and then thoroughly mixed to ensure even distribution of the fluorescein dye. A 50.0 g aliquot from each sample section was removed and placed into a one liter Erlenmeyer flask. 150 ml of 0.001 N NaOH in methanol was added to the sample and the mixture was stirred vigorously for 2-3 minutes. The solid material present in the flask was separated from the liquid by suction filtration and then washed with 10 ml of 0.001 N NaOH in methanol. The NaOH/methanol wash was added to the filtrate. The solid was then washed twice with 150 ml aliquots of 0.001 N NaOH in methanol. The NaOH/methanol wash was then added to the filtrate. The filtrate was then diluted with 0.001 N NaOH in methanol to a volume of 500 ml and stirred. A sample was then analyzed spectrophotometrically using a linear absorbance spectrophotometer (Perkin-Elmer Coleman 44). The results of this analysis for each sample section are given in Table 1.

TABLE 1

Fluorescein in Recored Samples

| Ex. | | Sample Depth (Inches) | | | | | | | |
|---|---|---|---|---|---|---|---|---|---|
| | | 0-6 | 6-12 | 12-18 | 18-24 | 24-30 | 30-36 | 36-42 | 42-48 |
| 1 | ppm Fluorescein | 52.6 | 2.8 | 1.1 | 0 | 0 | 0 | 0 | 0 |
| 2 | ppm Fluorescein | 3.8 | 0 | 0 | 0 | 0 | 0 | 0 | 0 |
| 3 | ppm Fluorescein | 11.7 | 0 | 0 | 0 | 0 | 0 | 0 | 0 |
| 4 | ppm Fluorescein | 10.6 | 0 | 0 | 0 | 0 | 0 | 0 | 0 |
| 5 | ppm Fluorescein | 1.1 | 0 | 0 | 0 | 0 | 0 | 0 | 0 |
| 6 | ppm Fluorescein | 1.2 | 0 | 0 | 0 | 0 | 0 | 0 | 0 |
| 7 | ppm Fluorescein | 9.57 | 0 | 0 | 0 | 0 | 0 | 0 | 0 |
| 8 | ppm Fluorescein | 57.42 | 0 | 0 | 0 | 0 | 0 | 0 | 0 |
| 9 | ppm Fluorescein | 16.27 | 0 | 0 | 0 | 0 | 0 | 0 | 0 |
| 10 | ppm Fluorescein | 10.63 | 0 | 0 | 0 | 0 | 0 | 0 | 0 |
| 11 | ppm Fluorescein | 17.01 | 0 | 0 | 0 | 0 | 0 | 0 | 0 |
| 12 | ppm Fluorescein | 25.25 | 0 | 0 | 0 | 0 | 0 | 0 | 0 |

Although the invention has been described in detail in the foregoing figures and examples for the purpose of illustration, it is to be understood that such detail is solely for that purpose and that variations can be made therein without departing from the spirit and scope of the invention except as may be limited by the claims.

What is claimed is:

1. A soil sample recoring device comprising:
   (a) a base upon which a cutting tube assembly and a means for advancing a soil sample assembly tube are mounted,
   (b) a cutting tube having a diameter smaller than that of sample assembly tubes containing the soil sample to be recored which cutting tube is made of a durable material and has at one of its ends a collar assembly containing means for cutting away a soil sample-containing tube and the outer layer of the soil sample being recored which cutting tube remains stationary during operation,
   (c) a means for advancing a tube containing the soil sample to be recored in a manner such that a portion of the soil sample passes through the cutting tube and
   (d) a receptacle for the soil exiting the cutting tube.

2. The apparatus of claim 1 in which the cutting tube is made of stainless steel and the cutting means present in the collar assembly are knives.

3. The apparatus of claim 2 in which the tube containing the soil sample is a plastic tube which is held in place by a sample tube support until the advancing means (c) has advanced the soil sample through the cutting tube.

4. The apparatus of claim 3 in which the advancing means (c) is a hydraulic motor attached to the tube supports in a manner such that the sample containing tube will be advanced to pass through cutting tube (b) when the motor is activated.

5. The apparatus of claim 1 in which the tube containing the soil sample is a plastic tube which is held in position by a sample tube support until the advancing means (c) has advanced the soil sample through the cutting tube.

6. The apparatus of claim 1 in which the advancing means (c) is a hydraulic piston attached to the tube support in a manner such that the sample containing tube will be advanced to pass through cutting tube (b) when the motor is activated.

7. A method for recoring a soil sample using the apparatus of claim 1 in which a tube containing a soil sample is passed through the cutting tube (b) to obtain a recored sample which is collected intact in receptacle (d).

* * * * *